United States Patent [19]

Wang

[11] Patent Number: 4,800,231
[45] Date of Patent: Jan. 24, 1989

[54] KETO-DIESTERS PRODUCTION

[75] Inventor: Pen C. Wang, Houston, Tex.

[73] Assignee: Shell Oil Company, Houston, Tex.

[21] Appl. No.: 171,999

[22] Filed: Mar. 23, 1988

[51] Int. Cl.$^4$ ............................................. C07C 67/313
[52] U.S. Cl. ................................. 560/176; 560/54; 562/459; 562/578
[58] Field of Search ................. 560/54, 176; 562/459, 562/578

[56] References Cited

U.S. PATENT DOCUMENTS

| 2,533,944 | 12/1950 | Ladd | 560/178 |
| 3,840,587 | 10/1974 | Pearson | 560/210 |
| 4,165,438 | 8/1979 | Schneider | 560/211 |
| 4,560,790 | 12/1985 | Ryu | 560/211 |
| 4,581,471 | 4/1986 | Barlow et al. | 560/210 |

FOREIGN PATENT DOCUMENTS 088149  6/1982  Japan .

OTHER PUBLICATIONS

Organic Syntheses (1987), vol. 63, pp. 26–31.
Chem. Ber. (1976), 109, pp. 3426–3431.
Chem. Ber. (1980), 113, pp. 690–698.
Chem. Ber. (1981), 114, pp. 1226–1233.

Primary Examiner—Werren B. Lone
Assistant Examiner—Vera C. Clarke

[57] ABSTRACT

Novel keto-diesters are produced by a 2:1 condensation of lower alkyl esters of $\alpha,\beta$-ethylenically unsaturated carboxylic acids and aldehydes having two hydrogen atoms as portions of a formyl group, in the presence of a thiazolium salt as catalyst and a tertiary amine.

8 Claims, No Drawings

KETO-DIESTERS PRODUCTION

FIELD OF THE INVENTION

This invention relates to certain novel ketoesters and to the process for the production of the ketoesters. More particularly, the invention relates to the production of certain novel ketodiesters by reaction of unsaturated carboxylic acid esters and aldehydes in the presence of a thiazolium salt as catalyst.

BACKGROUND OF THE INVENTION

Reaction of an aldehyde and unsaturated or acidic compounds in the presence of an initiator or catalyst is broadly old in the art with the type of product which results depending upon the particular chemical nature of the reactants and the type of catalyst or initiator which is employed. Ladd, U.S. Pat. No. 2,533,944, reacts certain propenyl compounds such as allyl acetate or diallyl ether with aldehydes such as formaldehyde or acetaldehyde to produce the corresponding keto- or formyl-substituted compound in the presence of free radical initiators such as peroxy compounds. The reaction products are largely one-to-one addition products of the aldehyde and the propenyl compound.

Ryu, U.S. Pat. No. 4,560,790, reacts saturated carboxylic acids or corresponding esters with formaldehyde to produce α,β-unsaturated acids or derivatives, e.g., methacrylic acid or methacrylate esters. The process utilizes a specially produced acidic phosphorus-oxygen composition as catalyst. Here also, a one-to-one product results. Schneider, U.S. Pat. No. 4,165,438, describes a similar process using a vanadium orthophosphate catalyst. A related process is shown by Barlow, et al, U.S. Pat. No. 4,581,471, wherein the 1:1 condensation is conducted in the vapor phase in the presence of a high silica crystalline aluminosilicate zeolite catalyst.

While the above processes are useful in increasing the functionality of the unsaturated or acidic reactant through the formation of 1:1 addition products, it would be useful to provide a reaction of unsaturated carboxylic acid esters and aldeydes wherein the condensation is in a ratio of greater than 1:1 and thereby produce functionally substituted products of increased functionality.

In a related reaction, Japanese published patent application No. 57 88,149 (1982) and copending U.S. patent application Ser. No. 923,988, filed Oct. 28, 1986, (K-0625) describe the production of 4-oxoheptandioic acid or 4-oxoheptandioate esters by reaction of acrylate esters, carbon monoxide and hydrogen.

SUMMARY OF THE INVENTION

The present invention provides a process for the production of certain keto-diesters, that is, esters having at least one keto group and two carboxylic acid ester groups. The present invention additionally provides a process for the production of the keto-diesters by reaction of unsaturated carboxylic acid esters with certain aldehydes to produce a 2:1 condensation product. Certain of the diesters are novel.

DESCRIPTION OF THE INVENTION

The process of the invention is the reaction of alkyl α,β-unsaturated carboxylate esters and an aldehyde having two hydrogen atoms present as part of a formyl group. The process is conducted in the presence of a thiazolium salt as catalyst and a tertiary amine catalyst promoter.

The alkyl α,β-unsaturated carboxylate ester is an alkyl ester of a 2-alkenoic acid of up to 14 carbon atoms inclusive wherein the alkyl is lower alkyl, i.e., alkyl of up to 4 carbon atoms inclusive. Illustrative of such alkenoic acid esters are methyl acrylate, butyl 2-octenoate, methyl crotonate, methyl 2-dodecenoate, ethyl methacrylate, ethyl 2-hexenoate, methyl 2-heptenoate, butyl acrylate and propyl methacrylate. Preferred esters are of the formula

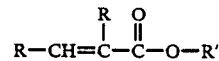

wherein R independently is hydrogen or methyl and R' is lower alkyl. The lower alkyl esters of acrylic acid and methacrylic acid are particularly preferred with best results obtained with methyl acrylate.

The aldehyde reactant is a mono- or dialdehyde of up to 12 carbon atoms inclusive, preferably up to carbon atoms inclusive, and characterized by the presence of 2 hydrogens each substituted on a carbon atom which is part of the carbon-oxygen double bond of a formyl group, i.e., a —CHO group. Such aldehydes are represented by the formula

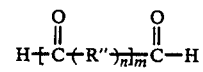

werein R" and n are as defined below and m is 0 or 1. The simplest member of this class of aldehydes, m=0, is formaldehyde which has only a single formyl group but two hydrogens present as a part of that group. Other members of the class are aliphatic or aromatic dialdehydes of the formula

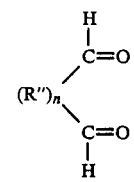

wherein R" is aliphatic or aromatic hydrocarbylene of up to 10 carbon atoms inclusive and n is 0 or 1. Preferred R" are aliphatic hydrocarbylene of up to 4 carbon atoms inclusive, for example, —CH$_2$—CH$_2$—. Illustrative of suitable aldehyde reactants are formaldehyde, glyoxal, succinaldehyde, octanedial, decanedial, 4-formylbenzaldehyde, 2-methyl-4-formyl-benzaldehyde and 1,5-diformylnaphthalene. Formaldehyde is a particularly preferred aldehyde reactant and is provided in any of the conventional forms including trioxane and paraformaldehyde. For other purposes, the dialdehyde reactants are preferred and the products of the dialdehyde reactants are novel.

The precise ratio of alkenoic acid ester to aldehyde reactants to be employed is not critical although a molar excess of ester is desired because of the 2:1 stoichiometry of the reaction. Molar ratios of alkenoic acid ester to aldehyde from about 1:1 to about 5:1 are satisfactory with molar ratios from about 1.5:1 to about 3:1 being preferred.

The catalyst employed in the process of the invention is a thiazolium salt. Without wishing to be bound by any particular theory, it is considered likely that the thiazolium moiety undergoes transitory participation through the 2-position and a hydrogen substituent on that 2-position. The substitution on the 4- and 5-carbon atoms of the thiazolium salt is not critical so long as the substituents are inert to the reactants and the condensation product thereof. The precise nature of the salt is also not critical although thiazolium halides are generally preferred thiazolium salts, particularly the middle halides, chlorides and bromides, and best results are obtained when a thiazolium chloride is utilized as catalyst. A typical and conventional thiazolium salt production involves the reaction of a thiazole and an alkyl, including arylalkyl, chloride. Formation of the salt serves to introduce the alkyl group of the alkyl chloride on the 3-position of the thiazole.

The preferred thiazolium salts are represented by the formula

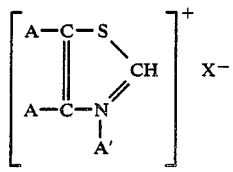

wherein X is middle halogen, preferably chlorine, A independently is hydrogen, alkyl of up to 8 carbon atoms, aryl of up to carbon atoms or 2-hydroxyethyl, and A' is alkyl including arylalkyl of up to carbon atoms.

Illustrative of suitable thiazole precursors of the tiazolium salt catalysts of the invention are thiazole, 4,5-dimethylthiazole, 4-methyl-5-(2-hydroxyethyl)-thiazole, 4-phenylthiazole, 5-methylthiazole and 4-methyl-5-benzylthiazole. Corresponding thiazolium salts which are suitably employed as the catalyst in the process of the invention include thiazolium hydrochloride, 3-benzyl-4,5-dimethylthiazolium chloride, 3,4,5-trimethylthiazolium bromide, 3-ethyl-4,5-diphenylthiazolium chloride, 3-benzyl-4-methyl-5-(2-hydroxyethyl)thiazolium chloride and 3,5-dibenzyl-4-methyl-thiazolium chloride. Such thiazolium salts are conventional and some are commercially available. Particularly preferred as the thiazolium salt is 3-benzyl-4-methyl-5-(2-hydroxyethyl)thiazolium chloride.

The thiazolium salt is employed in catalytic amounts, i.e., amounts which are less than stoichiometric with the ester and aldehyde reactants. Suitable amounts of thiazolium salt catalyst are from about 0.01 mole to about 0.5 mole per mole of thiazolium salt per mole of the aldehyde reactant, preferably from about 0.05 mole to about 0.3 mole of thiazolium salt per mole of aldehyde.

The tertiary amine catalyst promoter is a trialkylamine wherein each alkyl is alkyl of up to 12 carbon atoms inclusive but preferably at least two alkyls are lower alkyl. Illustrative of such trialkylamines are trimethylamine, triethylamine, trioctylamine, dimethyldodecylamine, dimethylethylamine, diisopropylbutylamine and methylethylpropylamine. Largely for convenience, the preferred trialkylamines are trimethylamine and triethylamine, particularly thiethylamine. The amine is employed in quantities which are approximately equimolar with the unsaturated ester. Quantities of tertiary amine catalyst promoter from about 0.7 mole to about 1.6 mole per mole of unsaturated ester reactant are satisfactory with quantities of amine from about 0.8 mole to about 1.2 mole per mole of ester reactant are preferred.

The condensation reaction of the invention is conducted in liquid phase solution in an inert reaction environment. Suitable as the reaction solvent are the lower alkanols such as mehtanol and ehtanol or aromatic hydrocarbon solvents such as toluene or xylene. The reactants are contacted in the presence of the catalyst and catalyst promoter by conventional methods such as stirring, shaking or refluxing. The use of an elevated reaction temperature is desired and reaction temperatures from about 35° C. to about 120° C. are suitable with temperatures from about 40° C. to about 100° C. being preferred. The reaction pressure to be employed is at least sufficient to maintain the reaction mixture in the liquid phase. Typical reaction pressures are from about 0.8 bar to about 10 bar, more typically from about 1 bar to about 3 bar. Subsequent to reaction the product mixture is separated and the desired keto-diester recovered by conventional methods such as distillation and selective extraction.

The keto-diester product of the invention is a 2:1 condensation product of the 2-alkenoic acid ester and the aldehyde. In terms of the preferred ester and aldehyde reactants, the keto diester product is represented by the formula

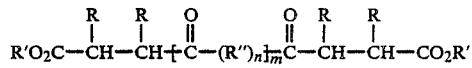

wherein R, R', R" and n have the previously stated meanings and m is 0 or 1.

By way of illustration, when the ester reactant is methyl acrylate and the aldehyde reactant is formaldehyde, each R of the above formula will be hydrogen, n and m each will be 0 and R' will be methyl. The resulting product is dimethyl 4-oxoheptandioate. When the 2-alkenoic acid ester is methyl methacrylate and the aldehyde is succinaldehyde, the resulting product will be dimethyl 2,9-dimethyl-4,7-dioxodecandioate. From the reaction of methyl acrylate and propandial is obtained dimethyl 4,6-dioxononandioate. Other products will be apparent from consideration of the above formula. Diesters produced from dialdehydes, i.e., the products of the above product formula wherein m is 1, are considered to be novel.

The products of the invention are polyfunctional α,Ω-diesters having ketone functionality in the central portion of the molecule and accordingly are useful as chemical intermediates for a number of applications. Particular applications include reaction with diamines to produce polyamides of structural similarity to the Nylons and reaction with diols to produce polyesters. Such polyamides or polyesters are thermoplastic polymers which are processed by conventional methods into sheets, films and molded articles having utility, inter alia, as packaging materials.

The invention is further illustrated by the following Illustrative Embodiments which should not be construed to be limiting.

ILLUSTRATIVE EMBODIMENT I

A solution of paraformaldehyde (9.0 g, 0.3 mole), 3-benzyl-5-(2-hydroxyethyl)-4-methylthiazolium chloride (16.0 g, 0.6 mole), triethylamine (36.0 g, 0.6 mole) and methyl acrylate (50.0 g, 0.58 mole) in 500 ml of ethanol was heated under nitrogen at 60°–70° C. for 24 hours. The solvent was then removed by distillation and the keto-diester was recovered by fractional distillation. The product, dimethyl 4-oxoheptanoate was characterized by a melting point of 49°–50° C. The portion and $C^{13}$ nuclear magnetic resonance spectra were consistent with the assigned structure.

ILLUSTRATIVE EMBODIMENT II

When the procedure of Illustrative Embodiment I is repeated employing an equivalent amount of succinaldehyde in place of the formaldehyde, a good yield of dimethyl 4,7-dioxodecandioate will be obtained.

What is claimed is:

1. A process for the production of keto-diesters by reacting a lower alkyl ester of a 2-alkenoic acid and an aldehyde having two hydrogen atoms present as part of a formyl group, in the presence of a thiazolium salt and a trialkylamine, in liquid phase solution.

2. The process of claim 1 wherein the aldehyde is of the formula

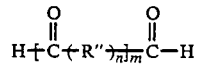

wherein n is 0 or 1, m is 0 or 1 and R'' is aliphatic or aromatic hydrocarbyl of up to 10 carbon atoms.

3. The process of claim 2 wherein the alkyl ester of 2-alkenoic acid is an alkyl ester of an alkenoic acid wherein the alkyl is lower alkyl and the alkenoic acid has up to 12 carbon atoms inclusive.

4. The process of claim 3 wherein the ester is of the formula

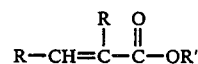

wherein R independently is hydrogen or methyl and R' is lower alkyl.

5. The process of claim 4 wherein the aldehyde is succinaldehyde.

6. The process of claim 4 wherein the aldehyde is formaldehyde.

7. The process of claim 6 wherein the ester is methyl acrylate.

8. The process of claim 6 wherein the ester is methyl methacrylate.

* * * * *